US006867199B2

(12) United States Patent
Rideout et al.

(10) Patent No.: US 6,867,199 B2
(45) Date of Patent: Mar. 15, 2005

(54) DINUCLEOSIDE POLYPHOSPHATE COMPOSITIONS AND THEIR THERAPEUTIC USE

(75) Inventors: Janet L. Rideout, Fuquay-Varina, NC (US); Benjamin R. Yerxa, Raleigh, NC (US); Sammy Ray Shaver, Chapel Hill, NC (US); James G. Douglass, III, Apex, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 10/425,847

(22) Filed: Apr. 28, 2003

(65) Prior Publication Data

US 2003/0207825 A1 Nov. 6, 2003

Related U.S. Application Data

(63) Continuation-in-part of application No. 09/817,017, filed on Mar. 23, 2001, now Pat. No. 6,555,675, which is a continuation-in-part of application No. 09/774,752, filed on Jan. 30, 2001, and a continuation-in-part of application No. 09/643,138, filed on Aug. 21, 2000.

(51) Int. Cl.[7] .......................... A61K 31/00; C07H 21/02
(52) U.S. Cl. ........................... 514/47; 514/51; 514/851; 514/378; 514/8; 514/912; 536/23.5; 536/26.23; 536/25.6; 424/46; 424/45; 424/489; 546/229
(58) Field of Search .......................... 514/47, 51, 851, 514/378, 8, 912; 536/23.5, 26.2, 25.6, 26.23; 424/46, 45, 489; 546/229

(56) References Cited

U.S. PATENT DOCUMENTS

| 4,855,304 A | 8/1989 | Devash ..................... 514/47 |
| 5,292,498 A | 3/1994 | Boucher .................... 424/45 |
| 5,635,160 A | 6/1997 | Stutts et al. ................ 424/45 |
| 5,681,823 A | 10/1997 | Kim et al. .................. 514/47 |
| 5,721,219 A | 2/1998 | Ingall et al. ................ 514/47 |
| 5,837,861 A | 11/1998 | Pendergast et al. ........ 536/25.6 |
| 5,900,407 A | 5/1999 | Yerxa et al. ................ 514/47 |
| 6,040,297 A | 3/2000 | De Flora .................... 514/47 |
| 6,159,952 A | 12/2000 | Shaffer et al. ............... 514/47 |
| 6,258,374 B1 * | 7/2001 | Friess et al. ............... 424/436 |
| 6,331,529 B1 | 12/2001 | Yerxa et al. ................ 514/47 |
| 6,458,946 B1 | 10/2002 | Maeda et al. ............. 536/26.21 |
| 6,555,675 B2 * | 4/2003 | Rideout et al. ............ 536/25.6 |
| 6,596,725 B2 | 7/2003 | Peterson et al. ............ 514/256 |
| 2002/0052336 A1 | 5/2002 | Yerxa et al. ................ 514/47 |
| 2002/0156269 A1 | 10/2002 | Maeda et al. ............. 536/26.21 |

FOREIGN PATENT DOCUMENTS

| EP | 1 191 032 A1 | 3/2002 | ........... C07H/19/10 |
| EP | 1 043 329 B1 | 8/2002 | ........... C07H/19/10 |
| SU | 689202 | 10/1993 | |
| WO | WO 96/02554 | 2/1996 | |
| WO | WO 96/40059 | 12/1996 | |
| WO | WO 98/15563 | 4/1998 | |
| WO | WO 98/34593 | 8/1998 | |
| WO | WO 98/34942 | 8/1998 | |
| WO | WO 98/55494 | 12/1998 | |
| WO | WO 99/05142 | 2/1999 | |
| WO | WO 00/30629 | 6/2000 | |
| WO | WO 01/87913 | 11/2001 | |
| WO | W0 02/096428 | 12/2002 | |

OTHER PUBLICATIONS

U.S. Appl. No. 09/570,231, Peterson, filed May 12, 2000.

Brown, et al., *Mol. Pharmocol.* 40, 648–55 (1991).

Burnstock, et al., "P2 purinergic receptors: Modulation of cell function and therapeutic potential," *Journal of Pharmacology and Experimental Therapeutics* 295(3) 862–869 (2000) XP002208652.

Drutz, et al., *Drug Dev. Res.* 37(3), 185 (1996).

Ferris, et al., "Oligomerization reactions of deoxyribonucleotides on montmorillonite clay: the effect of mononucleotide structure on phosphodiester bond formation," *Origins Life Evol. Biosphere,* 19(6):609–619 (1989) XP001085277.

Gobran, *Am. J. Physiol.* 267, L625–L633 (1994).

Guranowski, et al., *Nucleosides and Nucleotides* 14:731–734 (1995).

Lethem, et al., *Am. J. Respir. Cell Mol. Biol.* 9, 315–22 (1993).

Maminishkis, et al., "Purinoceptor agonists increase fluid clearance out of subretinal space (SRS) blebs in vivo," *IOVS,* 41(4):S136 (2000) XP001083820.

Mason, et al., *Br. J. Pharmacol.* 103, 1649–56 (1991).

Peterson, et al., "Extracellular ATP activates calcium signaling, ion, and fluid transport in retinal pigment epithelium," *Journal of Neuroscience,* 17:(7)2324–2337 (1997) XP001087693.

Scheffzek, et al., Crystal Structure of the Complex of UMP/CMP Kinase from *Dictyostelium discoideum* and the Bisubstrate inhibitor $P^1$–(5'–Adenosyl) $P^5$–(5'Uridyl) Pentaphosphate ($UP_5$ A) and $Mg^{2+}$ at 2.2A: Implications for Water–Mediated Specificity, *Biochemistry* 35:9716–9727 (1996).

(List continued on next page.)

*Primary Examiner*—James O. Wilson
*Assistant Examiner*—Devesh Khare
(74) *Attorney, Agent, or Firm*—Howrey, Simon, Arnold & White LLP; Viola T. Kung

(57) ABSTRACT

The present invention relates to certain novel dinucleoside polyphosphates of general Formulae I, II and III, and formulations thereof which are selective ligands of the P2Y purinergic receptors. Applicants have discovered that dinucleoside polyphosphates of general Formulae I, II and III are effective in clearing retained mucous secretions, balancing tissue hydration and fluid secretion, and/or inhibiting or preventing early stages of platelet activation, platelet degranulation, and platelet aggregation.

8 Claims, No Drawings

OTHER PUBLICATIONS

Sillero, et al., (2',3'–Dideoxynucleoside triphosphates (ddNTP) and di–2',3'–dideoxynucleoside tetraphosphates (ddNp4ddN) behave differently to the corresponding NTP and NP4N counterparts as substrates of firefly luciferase, and dinucleoside tetraphosphatase and phosphodiesterases, *Biochemica et Biophysica Acta* 1334(2–3):191–199 (1997) XP002208651.

Theoclitou, et al., "Characterization of stress protein LysU. Enzyme synthesis of diadenosine 5',5'–P1, P4–tetraphosphate (Ap4A) analogs by LysU," *J. Chem. Soc., Perkins Trans.* 1(16):2009–2019 (1996) XP00108769.

Visscher, et al. "Selective Cleavage of pyrophosphate linkages," *Nucleic Acids Research* 20(21):5749–5752 (1992).

* cited by examiner

DINUCLEOSIDE POLYPHOSPHATE COMPOSITIONS AND THEIR THERAPEUTIC USE

This application is a continuation-in-part of U.S. application Ser. No. 09/817,017, filed Mar. 23, 2001, U.S. Pat. No. 6,555,675; which is a continuation-in-part of U.S. application Ser. No. 09/643,138, filed Aug. 21, 2000, and U.S. application Ser. No. 09/774,752, filed Jan. 30, 2001. These and all other U.S. patents cited herein are hereby specifically incorporated herein by reference in their entirety.

TECHNICAL FIELD

The present invention relates to novel agents that are compositions of dinucleoside polyphosphates and analogues with purinergic receptor ligand activity, which facilitate secretory mechanisms, such as by increasing the hydration of mucus secretions, stimulating the production of mucins or fluids by cells and/or by increasing ciliary beat frequency to facilitate clearance of retained secretions, and/or which inhibit platelet activation, aggregation or degranulation.

BACKGROUND OF THE INVENTION

Chronic obstructive pulmonary disease (COPD) affects 15 million patients in the U.S. and is the sixth leading cause of death. It is characterized by the retention of mucus secretions in the lungs. Many patients diagnosed with COPD have a disorder called chronic bronchitis (CB), and 600,000 patients are hospitalized each year due to an acute exacerbation of CB. Cystic fibrosis and Primary Ciliary Dyskinesia (PCD) are other examples of lung disorders which assume a clinical profile similar to COPD. Ciliary dyskinesia, whether primary or secondary, results in retained secretions that can only be cleared by coughing.

Another disease state characterized by the accumulation of retained mucous secretions is sinusitis, an inflammation of the paranasal sinuses typically associated with an upper respiratory infection. Sinusitis is this country's most common health-care complaint, affecting an estimated 31 million people. (A. Moss and V. Parsons, National Center for Health Statistics, 1986: 66–7, DHHS Publication No. (PHS) 86–1588 (1985)).

Otitis media (OM) is a viral or bacterial infection of the middle ear, which primarily afflicts children under the age of three years. It is usually precipitated by an upper respiratory infection which spreads into the middle ear via the nasopharynx and eustachian tube. Approximately 25–50 million office visits are made each year for diagnosis and treatment of OM. By age three, about 75% of children will have had at least one episode of acute OM (J. Klein, Clin. Infect. Dis. 19, 823–33 (1994)). Following appropriate treatment with antibiotics, accumulated fluid in the middle ear remains, causing hearing impairment and potential language and cognitive development delays. Enhanced ability to clear secretions in the middle ear would reduce or eliminate significant sequelae of otitis media.

An additional disorder resulting from retained secretions is pneumonia. Patients who are immobilized for a variety of reasons are at high risk for developing pneumonia. Despite extra vigilance and numerous interventions, pneumonia develops in over 400,000 patients per year, with significant morbidity and mortality.

Mucous secretions are normally removed via the mucociliary clearance (MCC) system. MCC relies on the integrated action of three components: 1) mucus secretion by goblet cells and submucosal glands; 2) the movement of cilia on epithelial cells which propels the mucus across the luminal surface; and 3) ion transport into and out of luminal epithelial cells which concomitantly controls the flow of water into the mucus.

Similarly, disorders of secretion may lead to improper hydration at various body sites, thereby resulting in pathological conditions. These include dry eye disease, nasolacrimal duct obstruction, retinal detachment, glaucoma or ocular hypertension, retinal edema, retinal degeneration, improper joint lubrication, inflammatory diseases, vaginal dryness, gastroesophageal reflux, dry mouth, and constipation.

Enhancement of mucociliary clearance or balanced tissue hydration and fluid secretion would thus be useful in the prevention, management and treatment of such disorders. Furthermore, enhancement of mucociliary clearance would also have diagnostic applications such as sputum induction and detection of lung cancer.

It is now known that P2Y receptor agonists modulate many components of the MCC system by: (1) increasing both the rate and total amount of mucin secretion by goblet cells in vitro (Lethem, et al., *Am. J. Respir. Cell. Mol. Biol.* 9, 315–22 (1993)); (2) increasing cilia beat frequency in human airway epithelial cells in vitro (Drutz, et al., *Drug Dev. Res.* 37(3), 185 (1996)); (3) increasing $Cl^-$ secretion, hence, water secretion from airway epithelial cells in vitro (Mason, et al., *Br. J. Pharmacol.* 103, 1649–1656 (1991); and (4) releasing surfactant from Type II alveolar cells (Gobran, *Am. J. Physiol.* 267, L625-L633 (1994)). In addition to such actions, P2Y agonists have also been shown to increase intracellular $Ca^{++}$ due to stimulation of phospholipase C by the $P2Y_2$ receptor (Brown, et al., *Mol. Pharmacol.* 40, 648–655 (1991); Yerxa and Johnson, *Drugs of the Future* 24(7): 759–769 (1999)). U.S. Pat. Nos. 5,789,391; 5,763, 447; 5,635,160; 5,935,555; 5,656,256; 5,628,984; 5,902, 567; 5,292,498; 5,837,861; 5,900,407; 5,972,904; 5,981, 506; 5,958,897; 5,968,913; 6,022,527; 6,133,247; and 6,143,279, and PCT International Patents WO97/29756, WO97/35591, WO96/40059, WO97/05195, WO94/08593, WO98/19685, WO98/15835, WO98/03182, WO98/03177, WO98/34942, WO98/34593, WO99/09998, WO99/32085, WO99/61012, WO 00/30629, WO 00/50024, and WO96/40059 disclose beneficial therapeutic effects of certain dinucleotides and related compounds in sinusitis, otitis media, ciliary dyskinesia, pneumonia associated with immobilization, lung disease, cystic fibrosis, dry eye disease, vaginal dryness, bronchitis, edematous retinal disorders, retinal degeneration and detachment, and gastrointestinal disease. These and all other U.S. patents cited and herein are specifically incorporated herein by reference in their entirety.

Dinucleotides in the prior art are disclosed in the following references (International Patent Nos. WO96/40059, WO96/02554A1, WO-A-9815563, and WO98/55494; Theoclitou, et al., *J. Chem. Soc. Perkin Trans.* I, 2009–2019 (1996); Guranowski, et al., *Nucleosides and Nucleotides* 14, 731–734 (1995); Visscher, et al., *Nucleic Acids Research* 20, 5749–5752 (1992); Holler, et al., *Biochemistry* 22, 4924–4933 (1983); Orr, et al., *Biochem. Pharmacol.* 673–677 (1988); Plateau, et al., *Biochemistry* 24, 914–922 (1985); Hagmeier, et al., *J. Chromatography* 237, 174–177 (1982); Scheffzek, et al., *Biochemistry* 35, 9716–9727 (1996); Stridh, et al., *Antiviral Res.*, 97–105 (1981); Tarasova, et al., *Chem. Abs.* 110, 154770 (1988); Hata, et al., *Chem Lett.*, 987–990 (1976); Huhn, et al., 28, 1959–1970 (1993); Tumanov, et al., *Chem. Abs.* 109–6867d (1987);

Pintor, et al., *Molecular Pharmacology* 51, 277–284 (1997); and U.S. Pat. Nos. 4,855,304; 5,635,160; 5,495,550; and 5,681,823).

Applicants have discovered new dinucleoside compounds and analogues which are effective in clearing retained mucous secretions, balancing tissue hydration and fluid secretion, and/or inhibiting or preventing early stages of platelet activation, platelet degranulation, and platelet aggregation.

SUMMARY OF THE INVENTION

The invention provides novel pharmaceutical compositions comprising compounds of general Formula I, which feature: (1) a dinucleotide with a sugar moiety selected from the group consisting of: 3'-deoxyribofuranosyl, 2',3'-dideoxyribofuranosyl, arabinofuranosyl, 3'-deoxyarabinofuranosyl, xylofuranosyl, 2'-deoxyxylofuranosyl, and lyxofuranosyl (Formula I); (2) a dinucleotide analogue with an 8-azapurine base (Formula II); and (3) a dinucleotide analogue with a 6-substituted purine (Formula III).

The invention also provides methods for using such compounds in the clearance of retained mucous secretion, the enhancement of ciliary beat frequency, the restoration of proper tissue hydration, increased fluid secretion from intracellular areas into areas in need of such secretions or lubrication, and/or for inhibition of platelet activation, aggregation or degranulation processes in a subject or blood or plasma sample where such treatment would be beneficial. Accordingly, a broad embodiment of the invention is directed to compounds of general Formulae I, II and III, or the pharmaceutically acceptable non-toxic esters, amides, ureas, carbamates, ethers, acetals, ketals and/or salts thereof.

The compounds of the present invention are selective ligands of the P2Y purinergic receptor family; thus, they may be useful in the treatment of respiratory system disorders including chronic obstructive pulmonary diseases (chronic bronchitis, PCD, and cystic fibrosis), and may also be useful in the treatment of immobilized patients who are at risk for developing pneumonia. Furthermore, because of their general ability to clear retained mucus secretions and stimulate ciliary beat frequency, the compounds of the present invention may also be useful in the treatment of sinusitis and otitis media. Additionally, the compounds of the present invention can facilitate secretory mechanisms at other body sites, such as the eye, for the treatment of dry eye, retinal degeneration and detachment, and edematous retinal disorders; the gastrointestinal tract, for treatment of gastrointestinal disease and dry mouth; the joint tissues, for treatment of diseases related to insufficient joint lubrication; and vagina, for vaginal dryness. The compounds of this invention are also useful for treating diseases and disorders stemming from increased levels of platelet activation, aggregation or degranulation processes in a subject or blood or plasma sample where such treatment would be beneficial.

DETAILED DESCRIPTION OF THE INVENTION

The invention provides novel compositions of certain dinucleoside polyphosphate compounds and analogues, which may be used therapeutically as purinergic receptor ligands. The invention also provides methods for using such compositions to facilitate clearance of retained mucous secretions; for enhancement of ciliary beat frequency; for treatment or prevention of disorders or diseases related to improper joint lubrication; for treatment of sinusitis; for treatment of dry eye disease; for treatment of nasolacrimal duct obstruction; for treatment of retinal detachment; for treatment of glaucoma or ocular hypertension; and/or for treatment of retinal edema or retinal degeneration. In addition, these compositions are useful for the treatment or prevention of disease states related to platelet activation, platelet aggregation and degranulation, such as for use as antithrombotic agents, or in the treatment or prophylaxis of unstable angina, coronary angioplasty (PTCA), myocardial infarction, perithrombolysis, primary arterial thrombotic complications of atherosclerosis such as thrombotic or embolic stroke, peripheral vascular disease, myocardial infarction with or without thrombolysis, arterial complications due to interventions in atherosclerotic disease such as angioplasty, endarterectomy, stent placement, coronary and other vascular surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, heparin-induced thrombocytopaenia and pre-eclampsia/eclampsia, or venous thrombosis such as deep vein thrombosis, venoocclusive disease, and/or haematological conditions such as myeloproliferative disease, including thrombocythaemia. These compositions are also useful in the prevention or early reversal of mechanically-induced platelet activation in vivo, such as cardio-pulmonary bypass (prevention of microthromboembolism). Furthermore, these compounds are useful for inhibiting mechanically-induced platelet activation in vitro, such as for use in the preservation of blood products, e.g. platelet concentrates, or preventing or reducing shunt occlusion such as in renal dialysis and plasmapheresis; these compositions are also useful for treatment or prevention of thrombosis secondary to vascular damage/inflammation such as in vasculitis, arteritis, glomerulonephritis, inflammatory bowel disease and organ graft rejection, conditions such as migraine, Raynaud's phenomenon, atheromatous plaque formation/progression, vascular stenosis/restinosis and asthma, in which platelet-derived factors are implicated in the disease process. The method comprises administering to a mammal a pharmaceutical composition comprising a therapeutically effective amount of a P2Y receptor ligand. The "therapeutically effective amount" used herein means an amount effective to treat or prevent a disease, condition or disorder, which is an amount effective to inhibit or prevent, halt, or delay the progression of the disease state, or to confer protection from subsequent damage and degeneration. In the case of treatment of a plasma or blood sample to inhibit or reverse early stage platelet activation, aggregation or degranulation, the method comprises treatment of such a sample with an effective amount of a P2Y receptor ligand composition which causes the inhibition or prevention of early stage platelet activation, aggregation or degranulation.

This invention provides that P2Y receptors are localized to multiple cell types. Applicants believe that the interaction of P2Y receptors with the novel compounds of the present invention triggers specific cellular effects, which result in observed P2Y receptor-mediated therapeutic results.

A. New Sugar Moieties

P2Y ligands include dinucleoside polyphosphates as depicted by general Formula I, wherein one of the novel features is the presence of a sugar moiety selected from the group consisting of: 3'-deoxyribofuranosyl, 2',3'-dideoxyribofuranosyl, arabinofuranosyl, 3'-deoxyarabinofuranosyl, xylofuranosyl, 2'-deoxyxylofuranosyl, and lyxofuranosyl:

Formula I wherein:

X is oxygen, methylene, dihalomethylene (with difluoromethylene and dichloromethylene preferred), or imido;

n=0, 1 or 2;

m=0, 1 or 2;

n+m=0, 1, 2, 3, or 4;

Z=OH or H;

Z'=OH or H;

Y=OH or H;

Y'=OH or H; and

B and B' are each independently a purine residue or a pyrimidine residue, as defined in Formula Ia or Ib, linked through the 9- or 1-position, respectively;

Formula Ia wherein:

$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;

$R_2$ is hydroxy, alkenyl, oxo, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, or diacylamino, $R_x$ is O, H or is absent;

$R_2$ and $R_x$ are optionally taken together to form a 5-membered fused imidazole ring of 1, $N^6$-etheno adenine derivatives, optionally substituted on the 4- or 5-positions of the etheno moiety with alkyl, aryl or aralkyl moieties as defined below;

$R_3$ is hydrogen, azido, alkoxy, aryloxy, aralkyloxy, alkylthio, arylthio, or aralkylthio as defined below; or T($C_{1-6}$alkyl)OCONH($C_{1-6}$alkyl)W, wherein T and W are independently amino, mercapto, hydroxy or carboxyl; or pharmaceutically acceptable esters, amides or salts thereof; or absent;

J is carbon or nitrogen, with the provision that when J is nitrogen, $R_3$ is not present;

wherein the alkyls are straight-chain, branched or cyclic;

wherein the aryl groups are optionally mono-, di-, or tri-substituted with lower alkyl, aryl, amino, mono- or dialkylamino, $NO_2$, $N_3$, cyano, carboxylic, amido, sulfonamido, sulphonic acid, phosphate, or halo group;

Formula Ib wherein:

$R_4$ is hydroxy, oxo, mercapto, thione, amino, cyano, $C_{7-12}$arylalkoxy, $C_{1-6}$ alkylthio, $C_{1-6}$ alkoxy, $C_{1-6}$ alkylamino or di$C_{1-4}$alkylamino, wherein the alkyl groups are optionally linked to form a heterocycle;

$R_5$ is hydrogen, acetyl, benzoyl, $C_{1-6}$ alkyl, $C_{1-5}$ alkanoyl, aroyl, or absent;

$R_6$ is hydroxy, oxo, mercapto, thione, $C_{1-4}$alkoxy, $C_{7-12}$arylalkoxy, $C_{1-6}$alkylthio, S-phenyl, arylthio, arylalkylthio, triazolyl, amino, $C_{1-6}$alkylamino, $C_{1-5}$ disubstituted amino, or di-$C_{1-4}$alkylamino, wherein said dialkyl groups are optionally linked to form a heterocycle or linked to form a substituted ring such as morpholino, pyrrolo, etc.; or $R_5$ and $R_6$ taken together form a 5-membered fused imidazole ring between positions 3 and 4 of the pyrimidine ring and form a 3,$N^4$-ethenocytosine derivative, wherein said etheno moiety is optionally substituted on the 4- or 5-positions with $C_{1-4}$ alkyl, phenyl or phenyloxy; wherein at least one hydrogen of said $C_{1-4}$ alkyl, phenyl or phenyloxy is optionally substituted with a moiety selected from the group consisting of halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di-$C_{1-4}$ alkylamino, wherein said dialkyl groups are optionally linked to form a heterocycle;

$R_7$ is selected from the group consisting of hydrogen, hydroxy, cyano, nitro, $C_{1-6}$ alkyl or phenyl; substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, or propenoic acid and $C_{2-8}$ alkenyl; or $R_6$ and $R_7$ together form a 5 or 6-membered saturated or unsaturated ring bonded through N or O or S at $R_6$, such ring optionally contains substituents that themselves contain functionalities; and $R_8$ is selected from the group consisting of hydrogen, amino, di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, and phenylthio; provided that when $R_8$ is amino or substituted amino, $R_7$ is hydrogen.

The furanosyl moieties are as depicted in the D-configuration, but may be L-, or D- and L-. The D-configuration is preferred. The nucleoside residue can be in the alpha- or beta- and D- or L-configurations, but most preferably the beta-D-configuration;

The substituted derivatives of adenine include adenine 1-oxide; 1,$N^6$-(4- or 5-substituted etheno) adenine; $N^6$-substituted adenine; $N^6$-substituted 8-azaadenine; or $N^6$-substituted 8-aminoadenine, where R' of the 6- or 8-HNR' groups are chosen from among: arylalkyl ($C_{1-6}$ alkylene) groups or arylcycloalkyl ($C_{1-6}$ cycloalkylene) groups with said aryl moiety optionally functionalized as described below; alkyl; and alkyl groups with functional groups therein, such as: ([6-aminohexyl]carbamoylmethyl)-, and ω-acylated-amino(hydroxy, thiol and carboxy)alkyl($C_{2-10}$)- and their ω-acylated-amino (hydroxy, thiol and carboxy) derivatives where the acyl group is chosen from among, but not limited to, acetyl, trifluoroacetyl, benzoyl, substituted-benzoyl, etc., or the carboxylic moiety is present as its ester or amide derivative, for example, the ethyl or methyl ester or its methyl, ethyl or benzamido derivative. The ω-amino (hydroxy, thiol) moiety may be alkylated with a $C_{1-4}$ alkyl group.

B. Azapurine

Novel P2Y ligands also include dinucleoside polyphosphates as depicted by said general Formula II with the novel feature of an azapurine base, as described below. The nucleoside residue may include the glycone moieties: ribofuranosyl, 2'-deoxyribofuranosyl, 3'-deoxyribofuranosyl, 2', 3'-dideoxyribofuranosyl, arabinofuranosyl, 3'-deoxyarabinofuranosyl, xylofuranosyl, 2'-deoxyxylofuranosyl, lyxofuranosyl, and 2,3-dihydroxy-4-methyleneoxy-cyclopentane. The furanosyl moieties can be in the alpha- or beta- and D- or L-configurations, but most preferably the beta-D-configuration. The cyclopentane moieties are most preferred in the 1,4-cis configuration.

Formula II

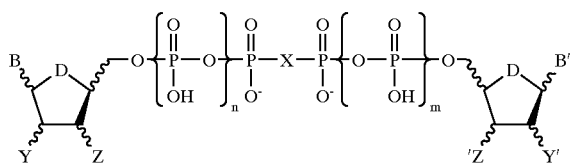

wherein:

D=O or $CH_2$; and

X, n, m, n+m, Z, Z', Y, and Y' are the same as described in Section A above.

B is an 8-azapurine as defined in Formula IIa, and B' is any purine or pyrimidine residue, as defined in Formula Ia or Ib linked through the 9- or 1-position, Formula IIa

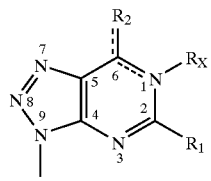

$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;

$R_2$ is hydroxy, oxo, alkenyl, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, or diacylamino;

$R_2$ is preferably mercapto, thione, alkylthio, arylthio, aralkylthio, acylthio, alkyloxy, aryloxy, aralkyloxy, acyloxy, monosubstituted alkylamino, monosubstituted cycloalkylamino, monosubstituted aralkylamino, monosubstituted arylamino or disubstituted amino;

$R_x$ is O, H or is absent;

$R_2$ and $R_x$ are optionally taken together to form a 5-membered fused imidazole ring of $1,N^6$-etheno adenine derivatives, optionally substituted on the 4- or 5-positions of the etheno moiety with alkyl, aryl or aralkyl moieties as defined below;

wherein the alkyls are straight-chain, branched or cyclic;

wherein the aryl groups are optionally mono-, di-, or tri-substituted with lower alkyl, aryl, amino, mono- or dialkylamino, $NO_2$, $N_3$, cyano, carboxylic, amido, sulfonamido, sulphonic acid, phosphate, or halo groups.

C. 6-Substituted Purine

Novel P2Y ligands also include dinucleoside polyphosphates as depicted by said general Formula III with the novel feature of a 6-substituted purine base, as described below. The nucleoside residue may include a variety of glycone moieties, such as ribofuranosyl, 2'-deoxyribofuranosyl, 3'-deoxyribofuranosyl, 2',3'-dideoxyribofuranosyl, arabinofuranosyl, 3'-deoxyarabinofuranosyl, xylofuranosyl, 2'-deoxyxylofuranosyl, lyxofuranosyl, and 2,3-dihydroxy-4-methyleneoxy-cyclopentane. The furanosyl moieties can be in the alpha- or beta- and D- or L-configurations, but most preferably the beta-D-configuration. The cyclopentane moieties are most preferred in the 1,4-cis configuration.

Formula III

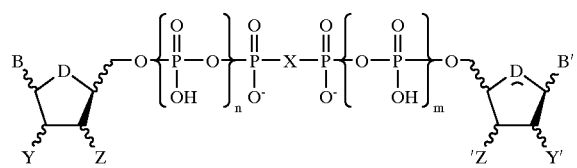

wherein:

X, D, n, m, n+m, Z, Z', Y, and Y' are the same as described in Section A and Section B above; and B is a purine residue as defined in Formula IIIa and B' is any purine or pyrimidine residue, as defined in Formula Ia or Ib, linked through the 9- or 1-position, respectively;

Formula IIIa

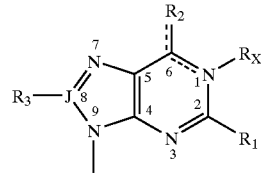

$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;

$R_2$ is mercapto, thione, alkylthio, arylthio, aralkylthio, acylthio, alkyloxy, aryloxy, aralkyloxy, acyloxy, monosubstituted cycloalkylamino, or di-substituted amino;

$R_x$ is O (adenine 1-oxide derivatives), H or is absent (adenine derivatives);

$R_3$ is hydrogen, azido, alkoxy, aryloxy, aralkyloxy, alkylthio, arylthio, or aralkylthio as defined below; or $T(C_{1-6}alkyl)OCONH(C_{1-6}alkyl)W$ wherein T and W are independently amino, mercapto, hydroxy or carboxyl, or pharmaceutically acceptable esters, amides or salts thereof;

J is carbon or nitrogen, with the provision that when J is nitrogen, $R_3$ is not present;

wherein the alkyls are straight-chain, branched or cyclic;

wherein the aryl groups are optionally mono-, di-, or tri-substituted with lower alkyl, amino, monoalkylamino, dialkylamino, $NO_2$, $N_3$, cyano, carboxylic, amido, sulfonamido, sulphonic acid, phosphate, or halo groups.

When at least one D=O in Formula II (azapurine) or Formula III (C6-substituted purine), the dinucleotide analogue contains a sugar moiety or furanosyl moiety. Each furanosyl moiety independently is selected from the group consisting of: ribofuranosyl, 2'-deoxyribofuranosyl, 3'-deoxyribofuranosyl, 2',3'-dideoxyribofuranosyl, arabinofuranosyl, 3'-deoxyarabinofuranosyl, xylofuranosyl, 2'-deoxyxylofuranosyl, and lyxofuranosyl. However, when at least one $D=CH_2$ in Formula II (azapurine) or Formula III (C 6-substituted purine), the dinucleotide analogue contains a cyclopentanyl derivative.

In the general structure of Formulae Ia, IIa and IIIa, the dotted lines are intended to indicate the presence of single or double bonds in these positions; the relative positions of the double or single bonds being determined by whether the $R_2$ and $R_x$ substituents are capable of keto-enol tautomerism.

In the general structure of Formulae Ib, IIb and IIIb, the dotted lines in the 2- to 6-positions are intended to indicate the presence of single or double bonds in these positions; the relative positions of the double or single bonds being determined by whether the $R_4$, $R_5$, $R_6$, $R_7$, and $R_8$ substituents are capable of keto-enol tautomerism.

In the general structures of Formula Ia, Ib, IIa, IIb, IIIa, and IIIb above, the acyl groups comprise alkanoyl or aroyl groups. The alkyl groups contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above-mentioned alkenyl and alkynyl groups contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are selected from halogen, hydroxy, $C_{1-4}$ alkoxy, $C_{1-4}$ alkyl, $C_{6-12}$ aryl, $C_{6-12}$ arylalkoxy, carboxy, cyano, nitro, sulfonamido, sulfonate, phosphate, sulfonic, amino and substituted amino wherein the amino is singly or doubly substituted by a $C_{1-4}$ alkyl, and when doubly substituted, the alkyl groups optionally being linked to form a heterocycle.

Suitable examples of specific compounds that fall within at least one embodiment of the present invention include: $P^1$-[(N6-phenyl)-8-azaadenosine 5'-]$P^4$-(uridine 5'-) tetraphosphate; $P^1$-[(N6-phenyl)-8-azaadenosine 5'-]$P^4$-(2'-deoxyuridine 5'-) tetraphosphate; $P^1$-[(N6-phenyl)-8-aza-2-chloroadenosine 5'-]$P^4$-(uridine 5'-) tetraphosphate; $P^1$-(2'-deoxyadenosine 5'-)$P^4$-[(N6-phenyl)-8-azaadenosine 5'-] tetraphosphate; $P^1$-[4-{7-(anilino)-3H-1,2,3-triazolo[4,5-d] pyrimidin-3-yl}-cyclopentane-2,3-dihydroxy-1-methoxy-] $P^4$-(uridine 5'-) tetraphosphate; and tetraphosphoric acid P,P'''-bis-(4-{7[2-(3,4-difluorophenyl)-cyclopropylamino]-5-propylsulfanyl-1,2,3-triazolo[4,5-d] pyrimidin-3-yl}-2,3-dihydroxy-cyclopentylmethyl}ester.

The present invention provides a pharmaceutical formulation comprising the compound or the pharmaceutically acceptable non-toxic esters, amides, ureas, carbamates, ethers, acetals, ketals, or salt thereof according to Formula I, II, or III, in a pharmaceutically acceptable carrier, in the form of an aqueous, a gel, a gel-like, or a solid formulation. In one embodiment of the invention, the pharmaceutical formulation is in the form of an aqueous solution and comprises physiologically safe excipients formulated to osmolarity The pharmaceutically acceptable carrier includes a physiologically compatible vehicle selected from the group consisting of: aqueous electrolyte solutions, polyethers, polyvinyls, polymers of acrylic acid, lanolin, and glucosaminoglycans.

Compounds of Formulae I, II and III can be made in accordance with known procedures described by Zamecnik, et al., *Proc. Natl. Acad. Sci.* USA 89, 838–42 (1981); and Ng and Orgel, *Nucleic Acids Res.* 15:3572–80 (1987), Pendergast, et al., U.S. Pat. No. 5,837,861, or variations thereof.

Compounds encompassed by the present invention can be prepared by condensation of a nucleoside mono-, di-, or triphosphate, activated with a condensing agent such as, but not limited to, carbonyldiimidazole or dicyclohexylcarbodiimide, with a second molecule of the same or a different mono-, di-, or triphosphate to form the desired dinucleotide polyphosphate. Another method of preparation is the sequential condensation of a nucleoside phosphate, activated as above, with a non-nucleoside mono-, di- or polyphosphate moiety, such as, but not limited to, a monophosphate or pyrophosphate anion to yield the desired dinucleotide polyphosphate, the non-isolated intermediate in such a case being a mononucleotide polyphosphate. Yet another preparative approach is the sequential condensation of a mono-, di- or polyphosphate moiety, activated as mentioned above, or in the form of an acid halide or other derivative reactive toward nucleophilic displacement, with a nucleoside phosphate or polyphosphate to yield the desired dinucleotide polyphosphate. The desired dinucleotide polyphosphate may be formed by modification of a pre-formed dinucleotide polyphosphate by substitution or derivatization of a moiety or moieties on the purine, pyrimidine or carbohydrate ring. Nucleoside phosphates used as starting materials may be commercially available, or may be made from the corresponding nucleosides by methods well known to those skilled in the art. Likewise, where nucleosides are not commercially available, they may be made by modification of other readily available nucleosides, or by synthesis from heterocyclic and carbohydrate precursors by methods well known to those skilled in the art. The compounds araATP and araCTP are available from Sigma (St. Louis, Mo.). Tetra-acetyl xylofuranose obtained from Pfanstiehl (Waukegan, Ill.) can be converetd to xylouridine by the method of Gosselin, et al. (*J. Med. Chem.* 29(2): 203–213 (1986)). Various lyxo and arabinofuranosyl pyrimidines can be synthesized by the method of Iwai, et al. (pp. 388–394, in *Synthetic Procedures in Nucleic Acid Chemistry*, Eds. W. Werner Zorbach and R. Stuart Tipson, Interscience Publishers, New York, (1968).

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The compounds of the present invention also encompass their non-toxic pharmaceutically acceptable salts, such as, but not limited to, an alkali metal salt such as sodium or potassium; an alkaline earth metal salt such as manganese, magnesium or calcium; or an ammonium or tetraalkyl ammonium salt, i.e., $NX_4^+$ (wherein X is $C_{1-4}$). The salts that have monovalent cations are preferred, with lithium, sodium, and potassium being most preferred. Pharmaceutically acceptable salts are salts that retain the desired biological activity of the parent compound and do not impart undesired toxicological effects. The present invention also encompasses the acylated prodrugs of the compounds disclosed herein. Those skilled in the art will recognize various synthetic methodologies which may be employed to prepare non-toxic pharmaceutically acceptable salts and acylated prodrugs of the compounds.

This invention further provides a method of using a pharmaceutical composition comprising P2Y receptor ligands for the treatment of a variety of disorders related to tissue fluid secretions, mucociliary clearance, and retinal degeneration; such disorders include, for example, chronic obstructive pulmonary disease, pneumonia, cystic fibrosis, bronchitis, sinusitis, otitis media, nasolacrimal duct obstruction, dry eye disease, edematous retinal disorders, retinal degeneration, vaginal dryness, dry mouth and gastrointestinal disease.

U.S. Pat. Nos. 5,292,498 and 5,635,160 disclose a method of hydrating mucous secretions in the lungs by administering UTP, related uridine phosphate compounds, and a dinucleotide, $A_2P_4$, for the treatment of cystic fibrosis. U.S. Pat. No. 5,763,477 teaches a method of treating pneumonia in immobilized patients by promoting drainage of mucous secretions in congested airways of such patients comprising the administration of uridine phosphates, including UTP and $U_2P_4$. U.S. Pat. No. 5,789,391 teaches a method of treating sinusitis by promoting drainage of congested mucous secretions in the sinuses of said patient comprising administering uridine phosphates, including UTP and $U_2P_4$. A method for treating dry eye disease by stimulating tear secretion comprising the administration of mono- and dinucleotides is disclosed in U.S. Pat. No. 5,900,407. U.S. Pat. No. 6,159,952 discloses a method for treating bronchitis, by promoting clearance of retained mucous secretions in the bronchi, bronchioles and small terminal airways comprising the administration of uridine phosphates including UTP and $U_2P_4$. WO 00/30629 discloses a method of treating vaginal dryness by stimulating cervical and vaginal secretions comprising the administration of ATP, CTP, UTP, and $U_2P_4$. WO97/29756 teaches a method of treating otitis media by administering UTP and related compounds in an amount effective to promote fluid drainage from the middle ear by hydrating mucous secretions in the middle ear and by increasing ciliary beat frequency in the middle ear and Eustachian tube. WO97/35591 discloses a method of treating ciliary dyskinesia by stimulating ciliary beat frequency to promote mucociliary or cough clearance of retained secretions in the lungs, sinuses, or ears of a patient by administering mono- and dinucleotide polyphosphates. WO98/15835 discloses a method of inducing sputum production or for diagnostic purposes or expectoration by administering uridine 5'-triphosphate (UTP), $P^1, P^{4-}$(uridine 5'-) tetraphosphate ($U_2P_4$) or related compounds. U.S. patent application Ser. No. 09/747,777 discloses a method of treating gastrointestinal diseases or disorders in which the mucosal barrier of the gastrointestinal tract is impaired by administering a mono- or dinucleotide polyphosphate in an amount effective to regulate mucous or mucin secretions or to correct abnormal fluid transport in the gastrointestinal system. U.S. patent application Ser. No. 09/570,231 discloses a method of treating retinal degeneration by administering mono- and dinucleotide polyphosphates in an amount effective to mount a neuroprotective effect on the retinal glial and neuronal cells. U.S. patent application Ser. No. 09/774,752 teaches a method of treating retinal detachment and retinal edematous disorders by stimulating the removal of extraneous intra-retinal or subretinal pathological fluid. U.S. patent application Ser. No. 09/512,867 discloses a method of stimulating mucosal hydration, treating dry eye, treating rhinosinusitis, treating dry mouth, treating corneal injury, and treating vaginal dryness by administering uridine diphosphate derivatives and certain dinucleotide triphosphate derivatives in an amount effective to increase hydration. U.S. Patent Application Ser. No. 60/171,710 discloses a method of treating gastrointestinal diseases or disorders in which the mucosal barrier of the gastrointestinal system is impaired, or in which the fluid transport across the lumenal tract is abnormal, by administering mono- and dinucleotide polyphosphates in an amount effective to regulate mucus or mucin secretions or correct abnormal fluid transport in the gastrointestical system. All the references cited above are specifically incorporated herein by reference in their entirety. This invention applies Applicants' novel compounds in the treatment of a variety of disorders as described in the above references.

The compounds of the present invention are selective ligands of the P2Y receptors. An embodiment of the present invention is the use of these novel compounds in the treatment of mammals including humans suffering from chronic obstructive pulmonary diseases such as chronic bronchitis, PCD, and cystic fibrosis, as well as the treatment or prevention of pneumonia, including pneumonia due to immobility. A further embodiment is the use of such novel compounds in the treatment of sinusitis, otitis media and nasolacrimal duct obstruction in mammals, including humans, because of their general ability to clear retained mucus secretions and stimulate ciliary beat frequency. Yet a further embodiment of the compounds of the present invention is their use for treating mammals including humans with dry eye, retinal degeneration and edematous retinal disorders, including retinal detachment. Another embodiment of the present invention is the use of these compounds in the treatment of vaginal dryness. Yet another embodiment of the present invention is their use in treating gastrointestinal disorders. A further embodiment of the present invention is their use in the treatment of glaucoma. To summarize, these purinergic receptor ligands can have beneficial therapeutic effects in sinusitis, otitis media, ciliary dyskinesia, pneumonia associated with immobilization, lung disease, cystic fibrosis, dry eye disease, vaginal dryness, bronchitis, edematous retinal disorders, retinal degeneration, detachment and edema, dry mouth and gastrointestinal disease.

Though the compounds of the present invention are primarily concerned with the treatment of human subjects, they may also be employed for the treatment of other mammalian subjects such as dogs and cats for veterinary purposes.

The compounds of general Formula I, II and III may be administered orally, topically, parenterally, by inhalation or spray, intra-operatively, rectally, or vaginally in dosage unit formulations containing conventional non-toxic pharmaceutically acceptable carriers, adjuvants and vehicles. The term topically as used herein includes patches, gels, creams, aerosols, ointments, or nose, ear or eye drops. The term parenteral as used herein includes subcutaneous injections, intravenous, intramuscular, intrasternal, intra-articular, intrathecal, and intravitreal injection or infusion techniques. In addition, there is provided a pharmaceutical formulation comprising a compound of general Formulae I, II and III, and a pharmaceutically acceptable carrier. One or more compounds of general Formulae I, II and III may be present in association with one or more non-toxic pharmaceutically acceptable carriers or diluents or adjuvants and, if desired, other active ingredients. One such carrier would be sugars, where the compounds may be intimately incorporated in the matrix through glassification or simply admixed with the carrier (e.g., lactose, sucrose, trehalose, mannitol) or other acceptable excipients for lung or airway delivery.

One or more compounds of general Formula I, II and III can be administered separately or together, or separately or together with mucolytics such as DNAse or acetylcysteine; agents used to treat and manage glaucoma, including anti-cholinesterase inhibitors, carbonic anhydrase inhibitors, osmotic agents, parasympathomimetic agents, sympathomimetic agents, prostaglandins, hypotensive lipids and beta-adrenergic agents; agents used to treat edematous retinal disorders, including corticosteroids, carbonic anhydrase inhibitors, anti-inflammatory agents (such as COX-2 inhibitors and non-steroidal anti-inflammatory agents), and pharmaceuticals that promote digestion of collagen and fibrous tissues that connect vitreous and retina; agents used to treat dry eye disease; agents used to manage corneal injury; agents used to treat dry mouth; agents used to treat sinusitis, otitis media, and nasolacrimal duct obstruction; agents used to treat pneumonia, cystic fibrosis, bronchitis, and other chronic obstructive pulmonary disease; agents used to treat vaginal dryness; anti-infective agents; and agents used for neuronal protection.

The pharmaceutical compositions containing compounds of general Formula I, II and III can be in a form suitable for oral use, for example, as tablets, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions; and such compositions may contain one or more agents selected from the group consisting of: sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous suspensions contain the active materials in admixture with excipients suitable for the manufacture of aqueous suspensions. Such excipients are suspending agents, for example: sodium carboxymethylcellulose, methylcellulose and sodium alginate. Dispersing or wetting agents may be a naturally-occurring phosphatide or condensation products of an allylene oxide with fatty acids, or condensation products of ethylene oxide with long chain aliphatic alcohols, or condensation products of ethylene oxide with partial esters from fatty acids and a hexitol, or condensation products of ethylene oxide with partial esters derived from fatty acids and hexitol anydrides. Those skilled in the art will recognize the many specific excipients and wetting agents encompassed by the general description above. The aqueous suspensions may also contain one or more preservatives, for example, ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Compounds of general Formulae I, II and III can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle. The sterile injectable preparation may be a sterile injectable solution or suspension in a non-toxic parentally acceptable diluent or solvent. Among the acceptable vehicles and solvents that may be employed are sterile water, saline solution, or Ringer's solution.

The compounds of general Formulae I, II, and III can also be administered in the form of suppositories for ear, rectal or vaginal administration of the drug. These compositions can be prepared by mixing the drug with a suitable non-irritating excipient, which is solid at ordinary temperatures but liquid at body temperature and will, therefore, melt to release the drug. Such materials are cocoa butter and polyethylene glycols.

Another means of administration of the active compounds is intra-operative instillation of a gel, cream, powder, foam, crystals, liposomes, spray or liquid suspension form of said compound, such that a therapeutically effective amount of said compound contacts the target site of said patient via systemic absorption and circulation.

Dosage levels of the order of from about $10^{-7}$ M to about $10^{-1}$ M, preferably in the range $10^{-5}$ to $10^{-1}$M, are useful in the treatment of the above-indicated conditions. The effective dose ranges between about 0.1 to about 1000 mg, preferably between about 0.1 to about 100 mg, and most preferably between about 0.5 to about 50 mg for single doses. The amount of active ingredients that may be combined with the carrier materials to produce a single dosage form will vary depending upon the host treated and the particular mode of administration. It will be understood, however, that the specific dose level for any particular patient will depend upon a variety of factors, including the activity of the specific compound employed, the age, body weight, general health, sex, diet, time of administration, route of administration, and rate of excretion, drug combination and the severity of the particular disease undergoing therapy.

A further embodiment of the invention is the use of specific dinucleoside polyphosphates as specific ligands for different subtypes of purinergic receptors. For example, dinucleoside tetraphosphates may have specificity and affinity for $P2Y_2$ and/or $P2Y_4$ receptors, whereas dinucleotide triphosphates have specificity for $P2Y_6$ receptors.

The invention is illustrated further by the following examples, which are not to be construed as limiting the invention in scope or spirit to the specific procedures described in them.

EXAMPLE 1

$P^1$-(8-Azaadenosine-5'-) $P^4$-(uridine-5'-) tetraphosphate

8-Azaadenosine monophosphate sodium salt (prepared from 8-azaadenosine by the method of Yoshikawa, et. al; *Tetrahedron Lett.*, 5065–5068 (1967)) is dissolved in water, applied to a column of Biorad AG-MP50 strong cation exchange resin in its tributylamine form, the column eluted with water, and the eluate lyophilized. The resulting tributylamine salt of 8-azaadenosine MP is condensed in DMF at 50° C. for 24h with uridine 5'-cyclic trimetaphosphate, which is prepared by activating UTP with dicyclohexylcarbodiimide (see example 1). The reaction mixture is evaporated under high vacuum overnight. The residue is dissolved in water, filtered to remove a little residual dicyclohexylurea, and purified by semipreparative ion-exchange chromatography (Hamilton PRP X-100 column, eluting with isocratic 1.0 M ammonium bicarbonate, 5 mL/min). The appropriate product fractions are collected, then evaporated and lyophilized to give the title compound. The isolated ammonium salt of the title compound is converted to the tetrasodium salt by dissolving in water and applying this solution to a column of Biorad AG-MP50 strong cation exchange resin in its hydrogen form. Elution with water is followed by adjusting the eluent pH to 8 with sodium hydroxide, then removal of solvent in vacuo.

EXAMPLE 2

$P^1$-(6-Mercaptopurine riboside 5'-) $P^4$-(uridine 5'-) tetraphosphate

6-Mercaptopurine riboside monophosphate sodium salt (prepared from 6-mercaptopurine riboside by the method of Yoshikawa, et al. (1967) (*Tetrahedron Lett.*, 5065–5068) is dissolved in water, applied to a column of Biorad AG-MP50 strong cation exchange resin in its tributylamine form, the column eluted with water, and the eluate lyophilized. The resulting tributylamine salt of 6-mercaptopurine riboside MP is condensed as above in DMF with uridine 5'-cyclic trimetaphosphate, which is prepared by activating UTP with dicyclohexylcarbodiimide (see example 1). After evaporating the DMF from the reaction mixture in vacuo, the residue is dissolved in water and purified by ion exchange chromatography on a Hamilton PRP X-100 column, eluting with isocratic 1.0 M ammonium bicarbonate, 5 mL/min and appropriate product fractions collected and lyophilized.

EXAMPLE 3

$P^1$-(6-Mercaptopurine riboside 5'-) $P^4$-(2'-deoxyuridine 5'-) tetraphosphate 6-Mercaptopurine riboside monophosphate sodium salt (prepared from 6-mercaptopurine riboside by the method of Yoshikawa, et al. (1967) (*Tetrahedron Lett.*, 5065–5068) is dissolved in water, applied to a column of Biorad AG-MP50 strong cation exchange resin in its tributylamine form, the column eluted with water, and the eluate lyophilized. The resulting tributylamine salt of 6-mercaptopurine riboside MP is condensed as above in DMF with deoxyuridine 5'-cyclic trimetaphosphate, which is prepared by activating dUTP (Sigma, St. Louis, Mo.) with dicyclohexylcarbodiimide (prepared analogously to UcTP, see example 1). After evaporating the DMF from the reaction mixture in vacuo, the residue is dissolved in water and purified by ion exchange chromatography on a Hamilton PRP X-100 column, eluting with isocratic 1.0 M ammonium bicarbonate, 5 mL/min and appropriate product fractions collected and lyophilized.

EXAMPLE 4

$P^1$-(4-Thiouridine 5'-) $P^4$-(arabinocytidine 5'-) tetraphosphate

4-Thiouridine monophosphate sodium salt (Sigma, St. Louis, Mo.) is dissolved in water and applied to a column of Biorad AG-MP50 strong cation exchange resin in its tributylamine form. The column is eluted with water and the eluate lyophilized. The resulting tributylamine salt of 4-thio-UMP is condensed in DMF as above with cytidine arabinoside 5'-cyclic trimetaphosphate, prepared by activation of araCTP (Sigma, St. Louis, Mo.) with dicyclohexylcarbodiimide (prepared analogously to UcTP, see example 1). After evaporating the DMF from the reaction mixture in vacuo, the residue is dissolved in water and separated by ion exchange chromatography on a Hamilton PRP X-100 column, eluting with isocratic 1.0 M ammonium bicarbonate, 5 mL/min. The appropriate product fractions are collected and lyophilized to give the title compound.

EXAMPLE 5

$P^1$-(2'-Deoxyadenosine 5'-) $P^4$-(6-thiohexylpurine riboside 5'-) tetraphosphate A solution of 2'-deoxyadenosine 5'-triphosphate (dATP, Sigma, St. Louis, Mo.) trisodium salt in water is passed through a column of BioRad AG-MP 50 strong cation exchange resin in its tributylamine form and eluted with distilled water. To this solution is added tributylamine and the suspension is shaken until the pH of the aqueous fraction has risen to 8. The layers are separated and the aqueous solution evaporated to small volume, then lyophilized. The residue is dissolved in dry DMF and the solvent is evaporated at 0.1 mmHg. Dicyclohexylcarbodiimide (DCC) is added to an aliquot of the foregoing dATP solution and the solution is stirred at room temperature for 30 min. The deposited dicyclohexylurea is removed by filtration, the reaction mixture is extracted with ether, and the residue is dissolved in dry DMF. Condensing this 2'-deoxyadenosine 5'-cyclic trimetaphosphate (dAcTP) and 6-thiohexylpurine riboside 5'-monophosphate (prepared from 6-thiohexylpurine riboside by the method of Yoshikawa, et. al; (1967) (*Tetrahedron Lett.*, 5065–5068) is as described above. After evaporating the DMF from the reaction mixture in vacuo, the residue is dissolved in water, filtered, and separated by ion exchange chromatography on a Hamilton PRP X-100 column, eluting with isocratic 1.0 M ammonium bicarbonate, 5 mL/min, 30 min. The appropriate product fractions are collected and lyophilized.

EXAMPLE 6

$P^1$-(6-Eicosanyloxypurine riboside 5'-) $P^4$-(uridine 5'-) tetraphosphate

6-Chloropurine riboside monophosphate sodium salt (prepared from 6-chloropurine riboside by the method of Yoshikawa, et al. (1967) (*Tetrahedron Lett.*, 5065–5068) is dissolved in water, applied to a column of Biorad AG-MP50 strong cation exchange resin in its tributylamine form, the column eluted with water, and the eluate lyophilized. The resulting tributylamine salt of 6-chloropurine riboside MP is condensed as above in DMF with uridine 5'-cyclic trimetaphosphate, which is prepared by activating UTP with dicyclohexylcarbodiimide (see example 1). After evaporating the DMF from the reaction mixture in vacuo, the residue is dissolved in water and purified by ion exchange chromatography on a Hamilton PRP X-100 column, eluting with isocratic 1.0 M ammonium bicarbonate, 5 mL/min followed by collecting and lyophilizing the product fractions. This tetraphosphate dinucleotide is dissolved in DMF and treated with the sodium salt of 1-eicosanol (Aldrich, Milwaukee, Wis.) at 40° C. for 48 h. All solvents are evaporated in vacuo and the residue purified by ion exchange chromatography on a Hamilton PRP X-100 column, eluting with isocratic 1.0 M ammonium bicarbonate, 5 mL/min. The appropriate product fractions are collected and lyophilized.

EXAMPLE 7

Preparation of $P^1$-[(6-phenylcyclopropylamino)-8-azaadenosine 5']-$P^4$-(uridine 5') tetraphosphate 5-Amino-4,6-dichloropyrimidine is reacted with an equimolar amount of 1-amino-2,3,5-tri-O-acetylribofuranose at elevated temperature in dimethylformamide. After workup and silica gel chromatography, the isolated product is dissolved in cold dilute acetic acid and is treated with an aqueous solution of sodium nitrite. The 8-azapurine nucleoside is isolated and purified and is treated with phenylcyclopropylamine in refluxing methanol. The resulting nucleoside is dried at elevated temperature under vacuum, then is dissolved in trimethylphosphate. 2,4,6-collidine is added, the reaction cooled, and phosphorous oxycloride is added slowly. After 4 hours the reaction is quenched by addition of triethylammonium bicarbonate and the product is isolated by preparative HPLC. This vacuum dried product is added to a solution of uridine 5'-triphosphate, which is pretreated with dicyclohexylcarbodiimide, in dimethylformamide at elevated temperature. The product is isolated after quenching with triethylammonium bicarbonate and purified by preparative HPLC.

The invention, and the manner and process of making and using it, are now described in such full, clear, concise and exact terms as to enable any person skilled in the art to which it pertains, to make and use the same. It is to be understood that the foregoing describes particular embodiments of the present invention and that modifications may be made therein without departing from the spirit or scope of the present invention as set forth in the claims. To particularly point out and distinctly claim the subject matter regarded as invention, the following claims conclude this specification.

We claim:

1. A compound of Formula II, or the pharmaceutically acceptable non-toxic esters, amides, ureas, carbamates, ethers, acetals, ketals and/or salts thereof:

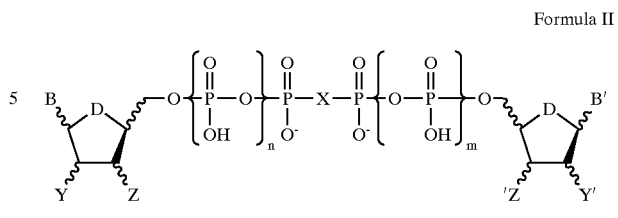

Formula II wherein:

D=O or $CH_2$;

X is oxygen, methylene, dihalomethylene, or imido;

n=0, 1 or 2;

m=0, 1 or 2;

n+m=0, 1, 2, 3 or 4;

Z=OH or H;

Z'=OH or H;

Y=OH or H;

Y'=OH or H; and

B and B' are each independently a purine residue or a pyrimidine residue, as defined in Formula IIa' or IIb, linked through the 9- or 1-position, respectively; and provided that at least one of B and B' is an 8-azapurine;

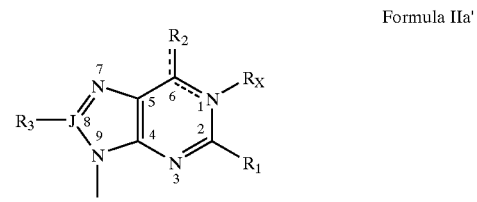

Formula IIa'

$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;

$R_2$ is hydroxy, alkenyl, oxo, amino, mercapto, thione, alkylthio, arylthio, aralkylthio, acylthio, alkyloxy, aryloxy, aralkyloxy, acyloxy, monosubstituted alkylamino, heterocyclic, monosubstituted cycloalkylamino, monosubstituted aralkylamino, monosubstituted arylamino, diaralkylamino, diarylamino, dialkylamino, acylamino, or diacylamino;

$R_x$ is O, H or is absent;

$R_2$ and $R_x$ are optionally taken together to form a 5-membered fused imidazole ring of 1,$N^6$-etheno adenine derivatives, optionally substituted on the 4- or 5-positions of the etheno moiety with alkyl, aryl or aralkyl moieties as defined below;

$R_3$ is absent, or is hydrogen, azido, alkoxy, aryloxy, aralkyloxy, alkylthio, arylthio, or aralkylthio as defined below; or $T(C_{1-6}alkyl)OCONH(C_{1-6}alkyl)W$ wherein T and W are independently amino, mercapto, hydroxy or carboxyl, or pharmaceutically acceptable esters, amides or salts thereof;

J is nitrogen or carbon;
provided that when J is nitrogen, $R_3$ is absent;

Formula IIb

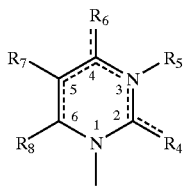

wherein:

$R_4$ is selected from the group consisting of: oxo, hydroxy, mercapto, thione, amino, cyano, $C_{7-12}$ arylalkoxy, $C_{1-6}$ alkylthio, $C_{1-6}$ alkoxy, $C_{1-6}$ alkylamino, and $diC_{1-4}$ alkylamino, wherein the alkyl groups are optionally linked to form a heterocycle;

$R_5$ is selected from the group consisting of hydrogen, oxo, acetyl, benzoyl, $C_{1-6}$ alkyl, $C_{1-5}$ alkanoyl, aroyl, and absent;

$R_6$ is selected from the group consisting of: hydroxy, oxo, mercapto, thione, $C_{1-4}$ alkoxy, $C_{7-12}$ arylalkoxy, $C_{1-6}$ alkylthio, amino, S-phenyl, arylthio, arylalkylthio, $C_{1-5}$ disubstituted amino, triazolyl, $C_{1-6}$ alkylamino, and di-$C_{1-4}$ alkylamino wherein said dialkyl groups are optionally linked to form a heterocycle or linked to form a substituted ring; or $R_5$ and $R_6$ taken together form a 5-membered fused imidazole ring of 3,$N^4$-ethenocytosine derivatives between positions 3 and 4 of the pyrimidine ring, wherein said etheno moiety is optionally substituted on the 4- or 5-positions with $C_{1-4}$ alkyl, phenyl, or phenyloxy; wherein at least one hydrogen of said $C_{1-4}$ alkyl, phenyl, or phenyloxy is optionally substituted with a moiety selected from the group consisting of: halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle;

$R_7$ is selected from the group consisting of hydrogen, hydroxy, cyano, nitro, $C_{1-6}$ alkyl, phenyl, substituted $C_{2-8}$ alkynyl, halogen, substituted $C_{1-4}$alkyl, $CF_3$, $C_{2-3}$ alkenyl, $C_{2-3}$ alkynyl, allylamino, bromovinyl, ethyl propenoate, propenoic acid, and $C_{2-8}$ alkenyl; or $R_6$ and $R_7$ together form a 5 or 6-membered saturated or unsaturated ring bonded through N or O or S at $R_6$, such ring optionally contains functional substituents; and $R_8$ is selected from the group consisting of: hydrogen, amino, di-$C_{1-4}$ alkylamino, $C_{1-4}$ alkoxy, $C_{7-12}$ arylalkoxy, $C_{1-4}$ alkylthio, $C_{7-12}$ arylalkylthio, carboxamidomethyl, carboxymethyl, methoxy, methylthio, phenoxy and phenylthio; provided that when $R_8$ is amino or substituted amino, $R_7$ is hydrogen;

wherein the alkyls are straight-chain, branched or cyclic;
wherein the alkyl and aryl groups are optionally substituted with lower alkyl, aryl, amino, mono- or dialkylamino, $NO_2$, $N_3$, cyano, carboxylic, amido, sulfonamido, sulphonic acid, phosphate, or halo groups.

2. A compound of Formula III, or the pharmaceutically acceptable non-toxic esters, amides, ureas, carbamates, ethers, acetals, ketals and/or salts thereof:

Formula III

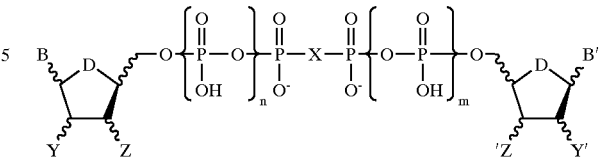

wherein:

D=O or $CH_2$;

X is oxygen, methylene, dihalomethylene, or imido;

n=0, 1 or 2;

m=0, 1 or 2;

n+m=0, 1, 2, 3 or 4;

Z=OH or H;

Z'=OH or H;

Y=OH or H;

Y'=OH or H; and

B and B' are each independently a purine residue or a pyrimidine residue, as defined in Formula IIIa or IIIb, linked through the 9- or 1-position, respectively; and provided that at least one of B and B' is a purine:

Formula IIIa

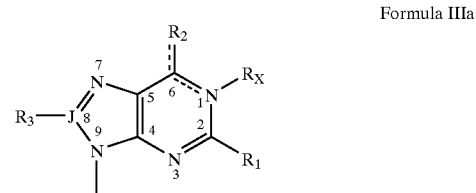

$R_1$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;

$R_2$ is mercapto, thione, alkylthio, arylthio, aralkylthio, acylthio, alkyloxy, aryloxy, aralkyloxy, acyloxy, monosubstituted cycloalkylamino, or di-substituted amino;

$R_x$ is O, H or is absent;

$R_3$ is hydrogen, azido, alkoxy, aryloxy, aralkyloxy, alkylthio, arylthio, or aralkylthio as defined below; or T($C_{1-6}$alkyl)OCONH($C_{1-6}$alkyl)W wherein T and W are independently amino, mercapto, hydroxy or carboxyl, or pharmaceutically acceptable esters, amides or salts thereof;

J is carbon or nitrogen, with the provision that when J is nitrogen, $R_3$ is not present;

Formula IIIb

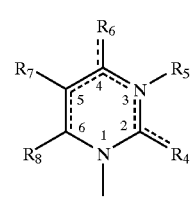

wherein:

$R_4$ is selected from the group consisting of: oxo, hydroxy, mercapto, thione, amino, cyano, $C_{7-12}$ arylalkoxy, $C_{1-6}$ alkylthio, $C_{1-6}$ alkoxy, $C_{1-6}$ alkylamino, and $diC_{1-4}$ alkylamino, wherein the alkyl groups are optionally linked to form a heterocycle;

$R_5$ is selected from the group consisting of: hydrogen, oxo, acetyl, benzoyl, $C_{1-6}$ alkyl, $C_{1-5}$ alkanoyl, aroyl, and absent;

$R_6$ is selected from the group consisting of: hydroxy, oxo, mercapto, $C_{1-4}$ alkoxy, $C_{7-12}$ arylalkoxy, $C_{1-6}$ alkylthio, amino, S-phenyl, arylthio, arylalkylthio, $C_{1-5}$ disubstituted amino, triazolyl, $C_{1-6}$ alkylamino, and di-$C_{1-4}$ alkylamino wherein said dialkyl groups are optionally linked to form a heterocycle or linked to form a ring; or $R_5$ and $R_6$ taken together form a 5-membered fused imidazole ring between positions 3 and 4 of the pyrimidine ring and form a 3,$N^4$-ethenocytosine derivative, wherein said etheno moiety is optionally substituted on the 4- or 5-positions with $C_{1-4}$ alkyl, phenyl or phenyloxy, wherein at least one hydrogen of said $C_{1-4}$ alkyl, phenyl or phenyloxy is optionally substituted with a moiety selected from the group consisting of: halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, and di-$C_{1-4}$ alkylamino wherein said dialkyl groups are optionally linked to form a heterocycle;

$R_7$ is selected from the group consisting of hydrogen, hydroxy, cyano, nitro, $C_{1-6}$ alkyl, phenyl, substituted $C_{2-8}$ alkynyl, halogen, substituted $C_{1-4}$alkyl, $CF_3$, $C_{2-3}$ alkenyl, $C_{2-3}$ alkynyl, allylamino, bromovinyl, ethyl propenoate, and propenoic acid, and $C_{2-8}$ alkenyl; or $R_6$ and $R_7$ together form a 5 or 6-membered saturated or unsaturated ring bonded through N or O or S at $R_6$, such ring optionally contains functional substituents that themselves contain functionalities; and $R_8$ is selected from the group consisting of hydrogen, amino, di-$C_{1-4}$alkylamino, $C_{1-4}$ alkoxy, $C_{7-12}$ arylalkoxy, $C_{1-4}$ alkylthio, $C_{7-12}$ arylalkylthio, carboxamidomethyl, carboxymethyl, methoxy, methylthio, phenoxy and phenylthio provided that when $R_8$ is amino or substituted amino, $R_7$ is hydrogen;

wherein the alkyls are straight-chain, branched or cyclic;

wherein the aryl groups are optionally substituted with lower alkyl, amino, monoalkylamino, dialkylamino, $NO_2$, $N_3$, cyano, carboxylic, amido, sulfonamido, sulphonic acid, phosphate, or halo groups.

3. The compound according to claim 1 or 2, wherein said compound is selected from the group consisting of $P^1$-[(N6-phenyl)-8-azaadenosine 5'-]$P^4$-(uridine 5'-) tetraphosphate; $P^1$-[(N6-phenyl)-8-azaadenosine 5']-$P^4$-(2'-deoxyuridine 5'-) tetraphosphate; $P^1$-[(N6-phenyl)-8-aza-2-chloroadenosine 5'-]$P^4$-(uridine 5'-) tetraphosphate; $P^1$-(2'-deoxyadenosine 5'-)$P^4$-[(N6-phenyl)-8-azaadenosine 5'-] tetraphosphate; $P^1$-[4-{7-(anilino)-3H-1,2,3-triazolo[4,5-d]pyrimidin-3-yl}-cyclopentane-2,3-dihydroxy-1-methoxy-] $P^4$-(uridine 5'-) tetraphosphate; and tetraphosphoric acid P,P'''-bis-(4-{7[2-(3,4-difluorophenyl)-cyclopropylamino]-5-propylsulfanyl-1,2,3-triazolo[4,5-d]pyrimidin-3-yl}-2,3-dihydroxy-cyclopentylmethyl} ester.

4. A pharmaceutical formulation comprising the compound or the pharmaceutically acceptable non-toxic esters, amides, ureas, carbamates, ethers, acetals, ketals, or salt thereof according to claim 1 or 2, in a pharmaceutically acceptable carrier, in the form of an aqueous, a gel, a gel-like, or a solid formulation.

5. The pharmaceutical formulation according to claim 4, wherein the pharmaceutical formulation is in the form of an aqueous solution and comprises physiologically safe excipients formulated to osmolarity between 250–350 mOsm and pH 5–9.

6. The pharmaceutical formulation according to claim 4, wherein said pharmaceutically acceptable carrier is a physiologically compatible vehicle selected from the group consisting of: aqueous electrolyte solutions, polyethers, polyvinyls, polymers of acrylic acid, lanolin, and glucosaminoglycans.

7. A method of treating a disease associated with a disorder of mucous hydration, secretion and clearance in a mammal in need thereof, comprising:

administering to said mammal a therapeutic effective amount of the compound according to claim 1 or 2.

8. A method of treating a disease associated with platelet activation, platelet aggregation or degranulation, in a mammal in need thereof, comprising:

administering to said mammal a therapeutic effective amount of the compound according to claim 1 or 2.

* * * * *